United States Patent
Ye (10) Patent No.: US 8,055,322 B2
(45) Date of Patent: Nov. 8, 2011

(54) ION SENSOR FOR LONG TERM USE IN COMPLEX MEDIUM

(75) Inventor: Qingshan Ye, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 464 days.

(21) Appl. No.: 12/035,052

(22) Filed: Feb. 21, 2008

(65) Prior Publication Data

US 2008/0161665 A1 Jul. 3, 2008

Related U.S. Application Data

(62) Division of application No. 10/903,377, filed on Jul. 30, 2004, now Pat. No. 7,373,195.

(51) Int. Cl.
*A61B 5/05* (2006.01)

(52) U.S. Cl. .................................... 600/348; 600/345

(58) Field of Classification Search .................. 600/309, 600/345, 348

See application file for complete search history.

(56) References Cited

U.S. PATENT DOCUMENTS

| | | | |
|---|---|---|---|
| 3,957,613 A * | 5/1976 | Macur | 204/412 |
| 4,743,352 A * | 5/1988 | Watkins-Pitchford | 204/406 |
| 4,891,125 A | 1/1990 | Schultz | |
| 4,906,348 A | 3/1990 | Taichi et al. | |
| 4,908,117 A | 3/1990 | Kinlen et al. | |
| 4,927,518 A | 5/1990 | Tauber et al. | |
| 4,980,043 A | 12/1990 | Tomita et al. | |
| 5,034,113 A | 7/1991 | Iwamoto | |
| 5,066,383 A | 11/1991 | Yamaguchi et al. | |
| 5,139,641 A | 8/1992 | Neukum | |
| 5,230,786 A | 7/1993 | Preidel | |
| 5,234,570 A | 8/1993 | Taylor et al. | |

(Continued)

FOREIGN PATENT DOCUMENTS

EP 00247535 B1 9/1992

(Continued)

OTHER PUBLICATIONS

Vogt S. et al., "Tierexperimentelle Studie Zum Aufbau Von Mikroelektroden Fuer Den Selektiven Nachweis Von Epikardialen Kaliumionenaktivitaeten. Experimental Study on Microelectrodes for the Selective Detection of Epicardial Potassium Ion Activities", Biomedizinische Technik, Fachverlag Schiele Und Schoen Gmbh., 43(10), pp. 293-298 (1998).

Stiefel, Michael et al., "Cation dysfunction associated with cerebral ischemia followed by reperfusion: A comparison of microdialysis and ion-selective electrode methods", Journal of Neurosurgery, 97(1), pp. 97-103 (2002).

(Continued)

*Primary Examiner* — Charles A Marmor, II
*Assistant Examiner* — Karen Toth
(74) *Attorney, Agent, or Firm* — Reed A. Duthler; Stephen W. Bauer (57) ABSTRACT

Devices and methods for measuring a target ion concentration uses an electrode pair. The pair includes a working electrode and a reference electrode. The working and reference electrodes are ion-selective electrodes (ISEs). The reference ISE can include a sodium ISE. The ISE pair interacts with body fluids where a target ion concentration changes more than sodium ion concentration over time. Some ISE membranes of a pair vary essentially only in the ionophore. An ISE pair can determine the ratio of a target ion concentration to sodium ion concentration in vivo. Periodic measurement of sodium concentration in drawn blood can be used to calibrate an ISE pair and provide target ion concentration as an output. Or, a potassium/sodium ISE pair beneficially monitors potassium concentration changes over time in heart- or kidney-failure patients. Then, manual or automatic titration of a diuretic material can be implemented to maintain a desired potassium concentration.

6 Claims, 6 Drawing Sheets

U.S. PATENT DOCUMENTS

| | | | |
|---|---|---|---|
| 5,334,305 A | 8/1994 | Okada et al. | |
| 5,360,529 A | 11/1994 | Edwards et al. | |
| 5,470,453 A | 11/1995 | Nipkow et al. | |
| 5,951,473 A * | 9/1999 | Sherry et al. | 600/420 |
| 6,419,809 B1 | 7/2002 | Suzuki et al. | |
| 6,492,179 B1 * | 12/2002 | Bar-Or et al. | 436/74 |
| 6,554,982 B1 | 4/2003 | Shin et al. | |
| 6,616,821 B2 | 9/2003 | Broadley et al. | |
| 6,663,756 B2 | 12/2003 | Lee et al. | |
| 7,208,121 B2 | 4/2007 | Peper et al. | |
| 7,621,878 B2 * | 11/2009 | Ericson et al. | 600/561 |
| 2004/0039265 A1 * | 2/2004 | Bardy | 600/300 |
| 2004/0176672 A1 * | 9/2004 | Silver et al. | 600/345 |
| 2005/0049492 A1 * | 3/2005 | Sweeney et al. | 600/437 |
| 2006/0079740 A1 * | 4/2006 | Silver et al. | 600/309 |
| 2006/0155177 A1 * | 7/2006 | Phillips et al. | 600/310 |
| 2006/0191788 A1 * | 8/2006 | Wayment et al. | 204/403.01 |
| 2009/0137890 A1 * | 5/2009 | Burnes et al. | 600/365 |

FOREIGN PATENT DOCUMENTS

| | | |
|---|---|---|
| EP | 00313657 B1 | 5/1994 |
| EP | 00673506 B1 | 9/1994 |
| EP | 00682247 A1 | 11/1995 |
| EP | 01193495 A2 | 4/2002 |
| EP | 01343002 A2 | 9/2003 |
| JP | 61176846 | 12/1986 |
| WO | 9221960 A1 | 12/1992 |
| WO | 9417399 A1 | 8/1994 |
| WO | 9635116 A1 | 7/1996 |
| WO | 0054039 | 9/2000 |

OTHER PUBLICATIONS

Somps et al, "Electrochemical performance of an ion selective, polymeric membrane following chronic implantation in rat subcutaneous tissue," Sensors and Actuators B, 35(1-3), pp. 22-227 (1996).

Linder, et al., "Ion-Selective Membranes with Low Plasticizer Content: Electroanalytical Characterization and Biocompatability Studies," J. Biomed. Mat. Res., 28:591-601, (1994).

Simon et al., and D.M. Band, "Ion-selective electrodes and their clinical application in the continuous ion monitoring," Annals New York Academy of Sciences, vol. 428, 279-285 (1984).

Cosofret et al., "Electroanalytical and surface characterization of encapsulated implantable membrane planar microsensors," Analytica Chimica Acta, 314, pp. 1-11 (1995).

Dürselen et al., "Elimination of the asymmetry in neutral-carrier-based solvent polymeric membranes induced by proteins," Anal. Chem., 60, pp. 1455-1458 (1988).

Lim et al., "Continuous intravascular monitoring of epinephrine-induced changes in plasma potassium," Anesthesiology, 57(4), pp. 272-278 (1982).

Treasure, T. & Band, D. M., "A telemeter for ion selective catheter tipped electrodes," J. Med. Eng. Technol., 1, pp. 271-273 (1977).

Cosofret et al., "Ion-selective microchemical sensors with reduced preconditioning time, membrane biostability studies and applications in blood analysis," Analytical Letters, 27, pp. 3039-3063, (1994).

* cited by examiner

ION SENSOR FOR LONG TERM USE IN COMPLEX MEDIUM

CROSS REFERENCE TO RELATED APPLICATION

This application is a divisional application of U.S. patent application Ser. No. 10/903,377 filed Jul. 30, 2004 now U.S. Pat. No. 7,373,195, by Ye, now allowed.

FIELD OF THE INVENTION

The present invention is related generally to medical devices. More specifically, the present invention is related to ion-selective electrodes. The present invention can include an implantable electrode pair having a potassium ion-selective electrode as the working electrode and an implanted sodium ion-selective electrode as a reference electrode.

BACKGROUND OF THE INVENTION

Maintaining proper electrolyte concentration in the human body is not normally a concern in a majority of healthy people, and does not typically receive a great amount of general attention. The healthy human body is able to maintain an electrolyte balance within appropriate limits.

When, due to sudden illness, chronic illness, extreme diet, or medication, electrolytes become unbalanced, the result can be fatal. For example, when blood potassium concentration drops below a lower threshold, cardiac arrhythmia can occur, which can lead quickly to cardiac arrest and sudden death.

Heart failure is a chronic condition, in which the heart mechanically deteriorates over time. Heart failure can often be initiated by a non-fatal heart attack that kills cardiac muscle tissue, resulting in a weaker heart. The weaker heart does not pump as much blood with each stroke, leading to the heart enlarging to compensate in volume for the lack of strength.

The reduced pumping action of the heart can cause fluid to accumulate in the body, particularly in the extremities. In order to reduce the amount of fluid accumulation, heart failure patients are often prescribed diuretics, which reduce the amount of water maintained in the body. Diuretics work by regulating the excretion of water from the body through the kidneys. Increased water voiding reduces the amount of water held in the body, but can also increase the amount of potassium excreted, thereby decreasing the potassium concentration in the patient's blood. As previously described, low potassium levels can prove fatal.

Kidney disease patients may also be prescribed medications that alter the electrolyte balance. Even if not taking medication, patients having kidney problems may benefit from having electrolyte balance monitored. Examples of patients that would benefit from improved electrolyte monitoring include heart failure patients on ACE inhibitors and diuretics, hypertension patients, diabetes patients, kidney failure patients, and patients on dialysis.

Current patient management techniques may include visits to physicians or lab every other day to draw blood and measure electrolytes. Some single use, at home tests that require drawing blood (e.g. finger sticks) also exist. Applicant is not aware of any implantable, continuous potassium sensors currently available.

Many current cardiac rhythm management (CRM) products might be improved if biochemical sensors were incorporated, to either optimize the therapy or to measure physiologic variables for diagnostic purposes. In one example, related to heart failure, it has been found that the risk of both morbidity and death among patients with severe heart failure is reduced substantially, when aldosterone receptor antagonist-spironolactone is added to standard drug therapy (in conjunction with an ACE inhibitor and/or a loop diuretic). Higher doses of spirinolactone is needed to treat severe heart failure conditions. However, the higher the spirinolactone dose, the higher the risk of hyperkalimia. Thus it would be highly desirable to have an in vivo $K^+$ sensor to optimize spirinolactone dosing. In addition, if sensors were available for both $Na^+$ and $K^+$ to monitor kidney function, it would benefit heart failure disease management significantly, since the kidney is the main organ regulating body fluid excretion and balance.

Ion-selective electrodes (ISEs) have long been used to measure ion concentrations. One well-known ISE is a hydrogen ISE, typically known as a pH electrode. Other ISEs are also well known and commercially available. For example, ISEs exist which are selective for sodium ions. Sodium ISEs can be used on a bench top to measure sodium concentration in blood.

Electrochemical potentials are associated with electrochemical half-cell reactions. The half-cell reactions each have a potential relative to that of a standard half cell. Potentiometric ion-selective electrodes do not function by measuring absolute electrical potential. Rather, the ISE (the working electrode) and another electrode (the reference electrode) are coupled as a pair, and the differential electrical potential between the two is used as an indication of ion activity near the ISE.

The reference electrode used with an ISE is often a Ag/AgCl (metal/metal halide) electrode immersed in a saturated KCl solution, at defined concentration, pressure, and temperature. The KCl solution may in turn be immersed in, and in fluid communication with another solution, a salt bridge. The KCl can be depleted over time, and the KCl refilled through a port in the reference electrode designed for that purpose. The size of the KCl reservoir can be reduced, with an attendant reduction in time between required refills. This reference electrode is typically quite large, complicated to fabricate, and prone to drift in potential caused by samples and environment.

Current reference electrodes are thus not optimally suited for long term implantation. Applicant believes that both the reference electrode size and refill requirement has posed significant challenges to develop implantable ISEs, due to the need for a reference electrode, and the current lack of suitable implantable reference electrodes.

What would be desirable are small ISE electrode pairs suitable for implantation into a human body that do not require a conventional reference electrode.

SUMMARY OF THE INVENTION

The present invention provides methods for measuring a potassium ion concentration in a human body, where the method can include obtaining a differential electrical potential between an implanted potassium ion-selective electrode (ISE) and an implanted sodium ISE, then determining a sodium ion concentration near the sodium ISE. The method can also include determining a potassium ion concentration at least in part as a function of the sodium ion concentration and the differential electrical potential.

The method may also include determining the sodium ion concentration by measuring the sodium ion concentration in human body fluids. Some methods may include determining the sodium ion concentration using a function of at least the measured sodium ion concentration and a change in the differential electrical potential since the time of measuring the sodium ion concentration. Some methods include determining the sodium ion concentration by using an expected change based on therapy performed on the human body since the sodium measuring. The method may include determining the potassium ion concentration by application of a Nernst type equation utilizing the log of the ratio of the potassium and sodium ion activities. Body fluids that can be measured include blood, urine, and spinal fluid.

The present invention also provides methods for monitoring electrolyte changes in a human body fluid, where the method can include obtaining a differential electrical potential from an electrode pair implanted in the human body, the electrode pair including a potassium ion-selective electrode (ISE) and a sodium ISE. This method can also include obtaining a ratio of potassium ion concentration to sodium ion concentration at least in part as a function of the differential electrical potential.

The method can further include determining a sodium ion concentration from measuring sodium ion concentration in the human body fluid, and determining a potassium ion concentration at least in part as a function of the determined sodium ion concentration and the differential potential. The method may include repeating the obtaining step over time to monitor changes in the ratio over time. Some methods include generating an indication when the potassium to sodium ratio drops below a lower threshold.

One device according to the present invention is an implantable electrode pair including a potassium ion-selective working electrode and a sodium ion-selective reference electrode. The device may have the potassium ion-selective electrode including a first substrate, a first metal/metal-halide layer disposed on the first substrate, and a first potassium ISE membrane disposed over the metal/metal halide layer. The sodium ion-selective electrode can include a second substrate, a second metal/metal-halide layer disposed on the second substrate, and a second sodium ISE membrane disposed over the second metal/metal halide layer. A halide (reference electrolyte) containing layer may be interposed between the metal/metal-metal halide layer and the ISE membrane. The halide containing layer may be a hydrogel layer containing KCl as the reference electrolyte, disposed between the metal/metal halide layer and the ISE membrane.

In some devices, the implantable electrode pair first and second substrates are the same. The first and second metal/metal halide layer may have the same chemistry in some devices. The first ISE membrane may have a potassium ion-selective ionophore and the second ISE membrane may have a sodium selective ionophore, depending on the embodiment. In some devices, the first and second ISE membranes include a polymer in which the polymer is substantially the same for both ISE membranes.

In some electrode pairs, the first and second ISE membranes each include a mobile plasticizer in the polymer. In some electrode pairs, the first and second ISE membranes are self-plasticizing, having essentially no mobile plasticizer in the polymer. In some electrode pairs the potassium or target ion ISE and sodium ISE membranes are each contained within a surface area of less than about 1 square centimeter. In some implantable electrode pairs, the potassium and sodium ISE membranes each have no major dimension greater than about 1 centimeter.

Methods for monitoring a ratio of potassium ion to sodium ion concentration in blood in a human being over time are also included in the present invention. The method can include measuring a differential electrode potential between a potassium ISE and a sodium ISE both in contact with blood, obtaining the ratio at least in part as a function of the measured differential electrode potential.

Methods for controlling delivery of a substance into the human body are also included in the present invention. The methods can include measuring a differential potential from an ion selective electrode (ISE) pair implanted within the body, where the ISE pair includes a first ISE responsive to a first ion concentration electrically coupled to a second ISE responsive to a second ion concentration. The method can also include varying delivery of the substance at least in part as a function of the measured differential electrical potential.

In some methods, the first ion is potassium and the second ion is sodium, the first ISE is a potassium ISE, the second ISE is a sodium ISE, and the measuring includes measuring the differential electrical potential between the potassium ISE and the sodium ISE. The method may further include varying delivery by varying infusion from an implanted delivery device operably coupled to the ISE pair. In some methods, the substance includes a diuretic and the varied delivery includes varying delivery of the diuretic. The delivery device is located external to the body in some methods.

Implantable ion-selective electrode pairs are also within the scope of the invention. The ISE pairs can include a first substrate having a first electrical conductor in ion communication with a first ion-selective layer, in which the first ion-selective layer includes a first membrane (which may contain a first polymer) and a first ionophore, and in which the first membrane/polymer is self-plasticizing. The ISE pair can also include a second substrate having a second electrical conductor in ion communication with a second ion-selective layer, and in which the second ion-selective layer includes a second membrane (which may include a second polymer) and a second ionophore, in which the second membrane/polymer is self-plasticizing.

In some implantable ion-selective electrode pairs the first and second substrates are the same or substantially the same. In some ISE pairs, the first and second ISE membranes consist essentially of the same composition, but have different ionophores as between each other. The first and second ISE membranes may have different ionophore concentrations as between each other. In some ISE pairs, the first and second polymers are polymers with a polymer backbone and a plurality of pendant lipophilic plasticizing groups. The polymer may have a Tg of less than $-10°$ C. Some lipophilic plasticizing groups include C3-C7 or C3-C20 alkyl groups.

Some sodium ISEs exhibit a substantially sub-Nernstian response over a physiological range of sodium ion concentration, showing a less than Nerstian change in electrical potential with change in sodium concentration, thus providing a more constant reference electrode potential. Some sodium ISEs have a molar ratio of ionophore to lipophilic salt of between about 1 and 1.1.

The present invention also provides a method for detecting ischemia including obtaining a differential electrical potential between an implanted electrode pair in the human body, the electrode pair including a first ISE and a sodium ISE. The method can further include generating an indication of ischemia at least in part as a function of a change in the differential electrical potential over time. In some methods, the first ISE is a pH ISE, in which the change is a drop in pH over time. Some methods utilize a potassium ISE as the first ISE, where the change is a rise in a ratio of potassium to sodium over time. The electrode pairs can be implanted in the or near the heart or brain, to detect cardiac infarction or stroke, respectively.

DESCRIPTION OF VARIOUS EMBODIMENTS

Figure 1:
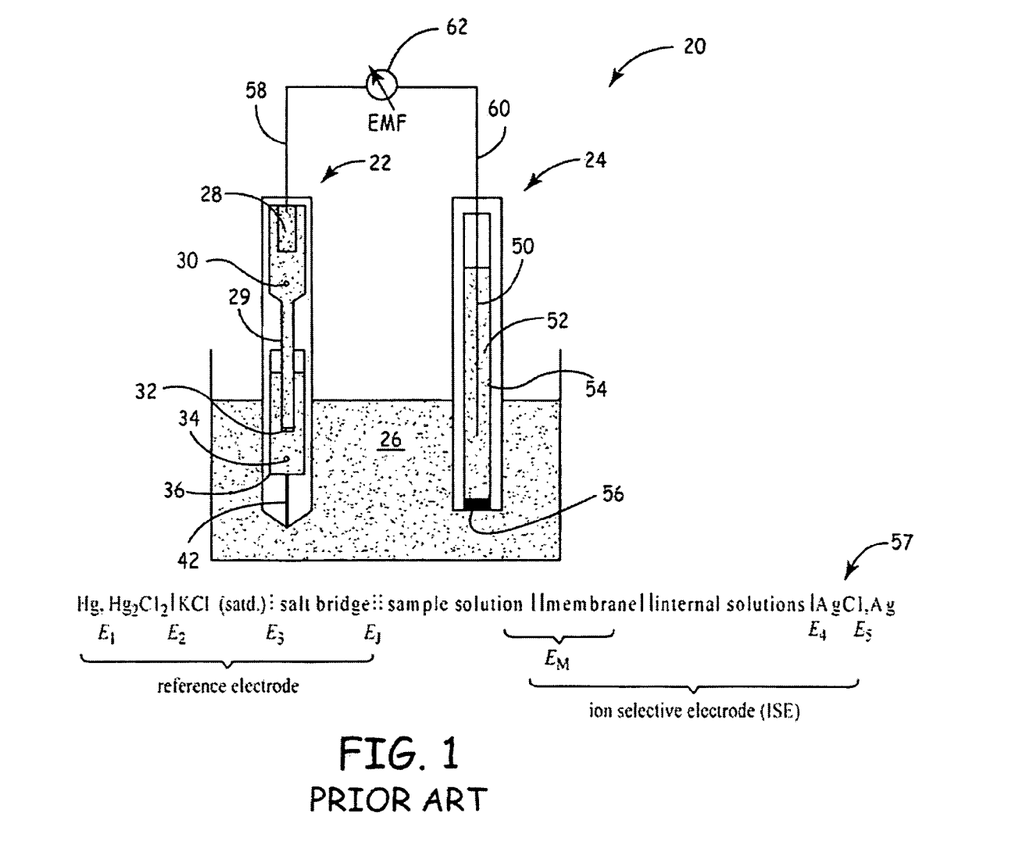
FIG. 1 is a schematic view of a prior art, bench top system for measuring ion activity using a working ISE and a reference electrode.

FIG. 1 illustrates a prior art, typical bench top potentiometric measurement setup 20, as is currently used to measure small ions such as $Na^+$, $K^+$ and $H^+$ using a potentiometric method. A specific ion activity is measured using a working ion-selective electrode (ISE) 24 against a reference electrode 22.

Ion-selective electrode 24 includes an internal electrode 50 having an Ag/AgCl (or $Hg/Hg_2Cl_2$) electrode immersed in an inner filling solution 52 contained within ISE vessel or chamber 54 and bounded by an ISE membrane 56, disposed between inner filling solution 52 and sample solution 26.

Working electrode 24 ISE membrane 56 is typically made of plasticized polymer membrane containing ionophore that is highly selective for the target ion being sensed. Different ion activity/concentration in sample solution 26 will produce different electrical potential on the working electrode membrane surface, and this potential has to be measured conventionally against reference electrode 22. The potential of reference electrode 22 should be constant and independent from changes of the sample ion activity/concentration.

Reference electrode 22 shown in FIG. 1 is of a frequently used design. Reference electrode 22 includes a $Hg/Hg_2Cl_2$ electrode 28 (which may be a Ag/AgCl electrode in other systems). $Hg/Hg_2Cl_2$ electrode 28 is immersed within a vessel or chamber 29 having a diaphragm 32 and containing saturated KCl as a reference electrolyte, indicated at 30. A salt bridge vessel or chamber 36 forms a salt bridge 34 containing a salt solution and extending through a capillary 42 into sample solution 26. A working electrode conductor 60 and a reference electrode conductor 58 allow the differential EMF to be measured as indicated at 62. The standard half-cell nomenclature for system 20 is given at 57.

To maintain the constant reference electrode potential, reference electrode 22 typically requires a constant $Cl^-$ concentration in inner reservoir 29 housing $Hg/Hg_2Cl_2$ electrode 28 (or a Ag/AgCl electrode instead), and also requires a constant flow of high concentration electrolyte (inner filling solution) such as KCl into the sample solution, to minimize the so-called liquid junction potential (LJP). A minimum flow rate is required to overcome counter diffusion of any interference ions into reference electrode chamber 29. A driving force like gravity or positive pressure is needed to maintain such a positive and constant flow. With a limited reservoir, frequent inner solution refilling of chamber 29 is necessary. To reduce the refilling frequency, a restriction element like a frit or porous membrane 32 is placed to lower the flow rate. However, dissolved salt from inner electrode 28 and protein or cells from sample solution 26 can block the porous structure of diaphragm 32 and thus introduce LJP variation, or even result in complete malfunction of reference electrode 22.

The size of the inner filling solution reservoir 29 cannot be too small, otherwise frequent refilling is still necessary even with restriction element 32 in place. This poses a great challenge to miniaturize the sensor system as a whole. Without the clogging or contamination of the restriction element, while under tight lab control on the bench, such a reference electrode can provide a constant potential reference within a 1 mV variation. This type of reference electrode is complicated in design, demands frequent maintenance, and is hard to miniaturize. Consequently, these difficulties present obstacles for in vivo applications, especially for chronic in vivo applications.

Figure 2:
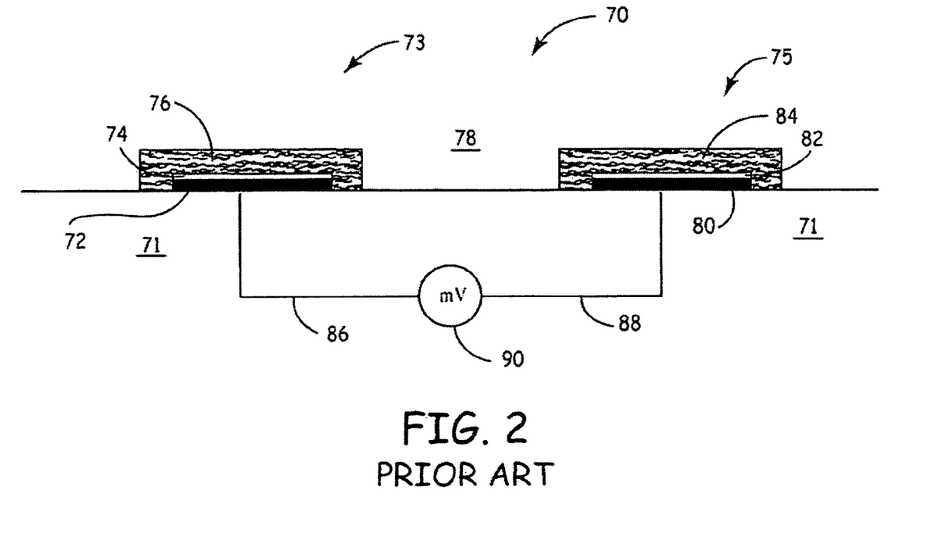
FIG. 2 is a schematic view of a prior art, thick film system for measuring ion activity using a working ISE and a reference electrode.

FIG. 2 illustrates another common prior art ISE system 70. System 70 includes a reference electrode 75 and a working electrode 73 for measuring ion activity in a sample solution 78, both based on thick films and both disposed on a substrate 71. Conductors 86 and 88 allow the differential electrical potential to be measured, as indicated at 90.

Working electrode 73 includes a Ag/AgCl layer 72 having a hydrogel layer 74 disposed over the Ag/AgCl layer. An ISE thick film membrane 76 is disposed over the hydrogel layer. Hydrogel layer 74 typically contains a fixed amount of electrolyte, e.g., KCl.

Reference electrode 75 includes a Ag/AgCl layer 80 having hydrogel layer 82 disposed over the Ag/AgCl layer. A non ion-selective porous membrane 84 is disposed on top of hydrogel layer 82. This non ion-selective porous membrane will act as restriction membrane to limit the exchange of ions from sample 78 into hydrogel layer 82, which would change the reference electrode potential, and to limit diffusion of the electrolyte incorporated in the hydrogel layer out of membrane 84 and into sample phase 78.

Sensor system 70 has been widely used for point of care electrolyte one-shot tests. Applicant believes that continuous use of this kind of sensor in complex media, like blood, serum or urine, or use inside tissue will face the same challenges of very limited reference electrode stability and short limited use life, owing to free diffusion of interfering ions from the sample into reference electrode membrane 84. In addition, since membranes 76 and 84 are made from different materials in most cases, the amount of protein absorption into them, and their adhesion to underlying hydrogel, etc. will be different. This different behavior can cause sensor signal drift, signal variation, or error. Applicant believes that this kind of sensor will not be able to function continuously for a long period of time, either in vivo or ex vivo, owing to its reference electrode limitations.

Another problem in using this type of sensor is frequent biofouling or limited biostability. In addition to protein absorption caused potential drift and/or signal error, when the ion sensor is in contact with blood or is implanted inside the body, thrombosis formation and tissue encapsulation may cause sensor unreliability and even malfunction. Thus, poor stability is a large problem, and should be significantly improved in order for ion sensors to be used long term in complex media like blood or urine, particularly in vivo.

Applicant believes that previous researchers and developers have been heavily influenced by conventional teaching, that a conventional reference electrode (e.g. AgCl or $Hg_2Cl_2$) is to be used for measuring ion activity using ISEs.

Figure 3:
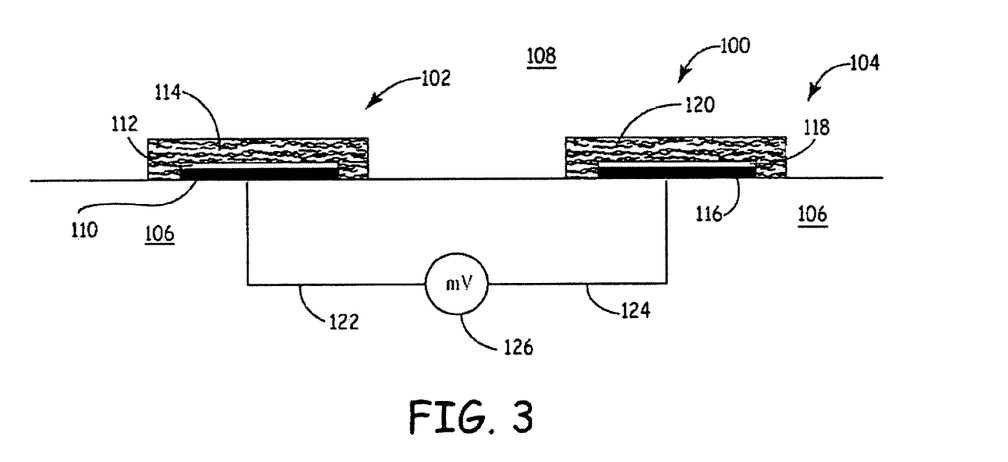
FIG. 3 is a schematic view of a thick film system of the present invention for measuring ion activity using a working ISE and a sodium ISE reference electrode.

FIG. 3 illustrates an ISE system 100 according to the present invention that does not require use of a conventional reference electrode. System 100 will be discussed below using the example of a system for measuring K+ ion activity in a sample 108, although the present invention is not limited to measuring the K+ ion. System 100 includes a working ISE 102 and a reference ISE 104 which may both be formed on a substrate 106 in some examples of the invention. Substrates may be polymeric, ceramic, or any other suitable material. Working electrode 102 can include a Ag/AgCl layer 110 having a hydrogel layer 112 disposed over the Ag/AgCl layer. Hydrogel layer 112 can contain a reference electrolyte, for example, KCl. An ISE membrane 114 can be disposed over the hydrogel layer. ISE membrane 114 can be selective for K+ ions.

Reference electrode 104 can include a Ag/AgCl layer 116 having a hydrogel layer 118 formed over the Ag/AgCl layer. Hydrogel layer 118 can contain a reference electrolyte, for example, KCl. A reference ISE membrane 120 can be formed over the hydrogel. Membrane 120 can be selective for Na+ ions. A working electrode conductor 122 can be coupled to Ag/AgCl layer 110 and a reference conductor 124 can be coupled to Ag/AgCl layer 116 to produce a differential electrical potential as indicated at 126.

Operation of the present invention may now be explained. Applying the well-known Nernst equation to the sodium (Na) and potassium (K) ion systems, we have:

$$\Delta E_{Na} = E_{Na}^0 + 59 * \log(a_{Na})$$

$$\Delta E_K = E_K^0 + 59 * \log(a_K)$$

therefore $$\Delta E_{K/Na} = E^{0'} + 59 * \log(a_K/a_{Na})$$

where $E^{0'} = E_K^0 - E_{Na}^0$

If the Na ion activity is relatively constant over time, or the relative change is small compared to the relative change of the K ion activity, then the K ion activity changes over time may be monitored using system 100 of FIG. 3. This is because the $\Delta E_{K/Na}$ will effectively track changes in $a_K$. If the Na ion activity is relatively constant over time and the Na ion activity can be periodically measured using conventional blood drawing and analytical techniques, then the absolute K ion activity may be accurately monitored by calibrating the system. Trending of K change is possible as it follows from the above equation that, for measurements taken at a time 1 and a time 2, that:

$$\Delta E_{2/1} = 59 * \log((a_{K2} \cdot a_{Na1})/(a_{K1} \cdot a_{Na2})) = \Delta E_{k2/k1} - \Delta E_{Na2/Na1} \quad \text{a.}$$

Hence a traditional reference electrode need not be used at all, instead a second ion-selective electrode will be used as a reference electrode. The potential change of the second ion-selective electrode should be small when using it in the intended application environment. The ratio of the ion pair, for example, Na/K, may itself be of high interest and clinical value, as in the case of kidney function monitoring. For example, normally sodium change in vivo will contribute to a much smaller potential change vs. the change of potassium, so the potassium change can be inferred indirectly from the $K^+/Na^+$ ratio measurement.

Blood sodium concentration normally can range from about 137 to about 148 mEq/L. Taking the ratio 148/137 and applying the Nernst equation, this corresponds to a band of about 2.7 mV. Blood potassium normally can range from between about 3.7 to 4.8 mEq/L. Taking the ratio 4.8/3.7 and applying the Nernst equation yields a band of about 12 mV. The absolute variability of the potassium concentration is less than that for sodium, but the relative variability is greater than that of sodium.

Therefore, even with some variation in sodium concentration, the log of the ratio of the concentration of potassium to sodium is still indicative of the potassium concentration. Trends in potassium concentration changes over time may be tracked using the K+/Na+ ratio obtained from the K+/Na+ ISE pair. Where only extremely low or extremely high K+ is important, the K+/Na+ ratio, together with an inferred, approximate, or previously measured Na+ concentration, can produce a clinically useful indication of a dangerous K+ level. Where the Na+ concentration can be accurately periodically obtained from bench top or at home measurements of drawn blood, then the K+/Na+ ratio provides a fairly accurate K+ concentration value.

The ISE pair values can be telemetrically transmitted from implanted medical devices to in-home patient management systems, which may be similar to those currently in use to monitor implanted cardiac pacing and monitoring systems over telephone lines.

The biofouling effect may also be minimized. Since the polymer matrix of the $K^+$ ion-selective membrane and the $Na^+$ ion-selective membrane can be almost identical, except for a difference in ionophore, the extent of protein adsorption and cell adhesion are expected to be almost equal, and the differential measurement scheme proposed here will cancel these effects out to a large extent. In contrast, in FIG. 2, the reference electrode membrane is a porous membrane and is typically quite different from the ion-selective membrane. For this reason, the biofouling process is expected to be quite different on the polymer membrane surfaces for the reference and working electrodes in FIG. 2.

The sensor drift can also be minimized. Sensor drift can be caused by polymer membrane deterioration, e.g., lipophilic salt leaching, neutral peptide/surfactant absorption, water absorption/swelling and adhesion to the substrate. This drift can be very similar for almost the identical polymer membranes of the two ISE membranes in FIG. 3. The two ISE membranes shown in FIG. 3 provide a differential measurement of the ion ratio (in this case $K^+/Na^+$), and can thus minimize this kind of drift, as the two membranes will likely be affected similarly. This drift has been very hard to be deal with when using a traditional reference electrode in the system.

The similarity of the two polymer membranes can also provide designs having easier construction. Construction of both the primary ion-selective sensor (the working electrode) and the secondary ion-selective sensor (the reference electrode) can be very similar.

Figure 4A:
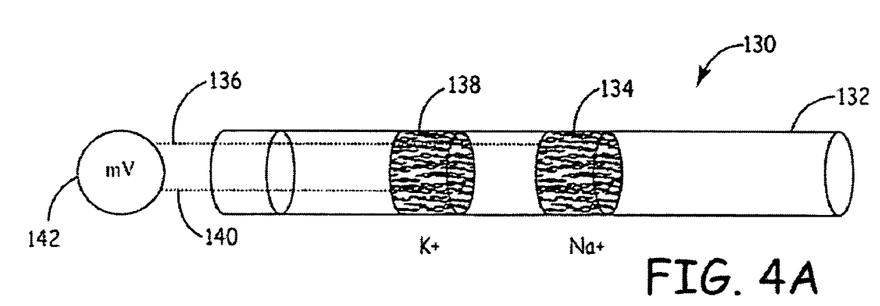
FIG. 4A is a schematic, perspective view of a lead having an ISE electrode pair including a sodium ISE as the reference electrode.

FIG. 4A illustrates a lead 130 including a lead shaft 132 having a symmetric sensor pair carrying a primary ISE 138 (the working electrode) for measuring K+ ion and a secondary ISE 134 (the reference electrode) for measuring sodium. Conductors 136 and 140 can carry the differential electrical signal from shaft 132 to be measured as indicated at 142. Applicant believes the symmetric sensor pair will be easier to manufacture than more dissimilar electrode pairs. The symmetric arrangement will help to reduce non-specific effects, such as drift or biofouling.

Figure 4B:
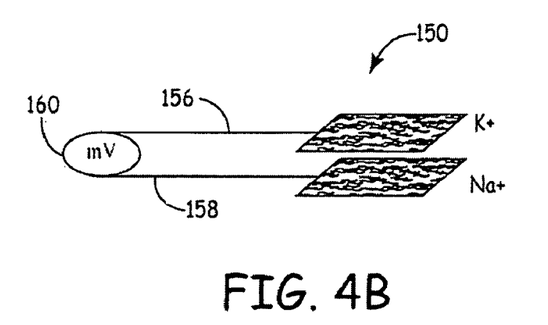
FIG. 4B is a schematic, perspective view of a lead having a planar ISE electrode pair including a sodium ISE as the reference electrode.

FIG. 4B illustrates another symmetric ISE pair 150 including a first planar ISE 152 for measuring K+ and a second ISE 154 for measuring Na+. The pair is coupled through conductors 156 and 158 to have the differential electrical potential measured as indicated at 160.

Figure 5A:
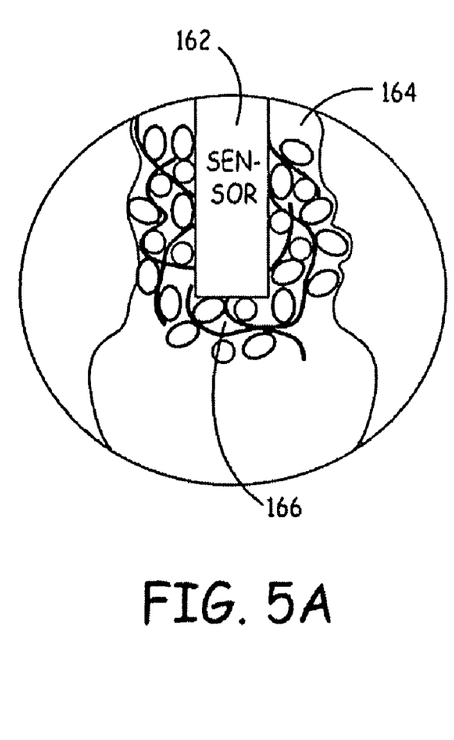
FIG. 5A is a detail view of an ISE pair sensor of the present invention disposed within a narrow body vessel having thrombus and a capsule formation near the sensor.

FIG. 5A illustrates an ISE pair 162 according to the present invention implanted in a narrow artery space 164. Thrombus formation and capsule formation is indicated at 166. In previous efforts, with traditional reference electrode designs, when an ion-selective sensor/biosensor was implanted in narrow artery space, the thrombosis formation and tissue encapsulation often caused both reference electrode and working electrode to not work properly, or to even stop functioning completely. Without the complication of the traditional reference electrode, the effect of thrombosis formation and tissue encapsulation is expected to be reduced or minimized, as previously explained, using some devices according to the present invention.

Figure 5B:
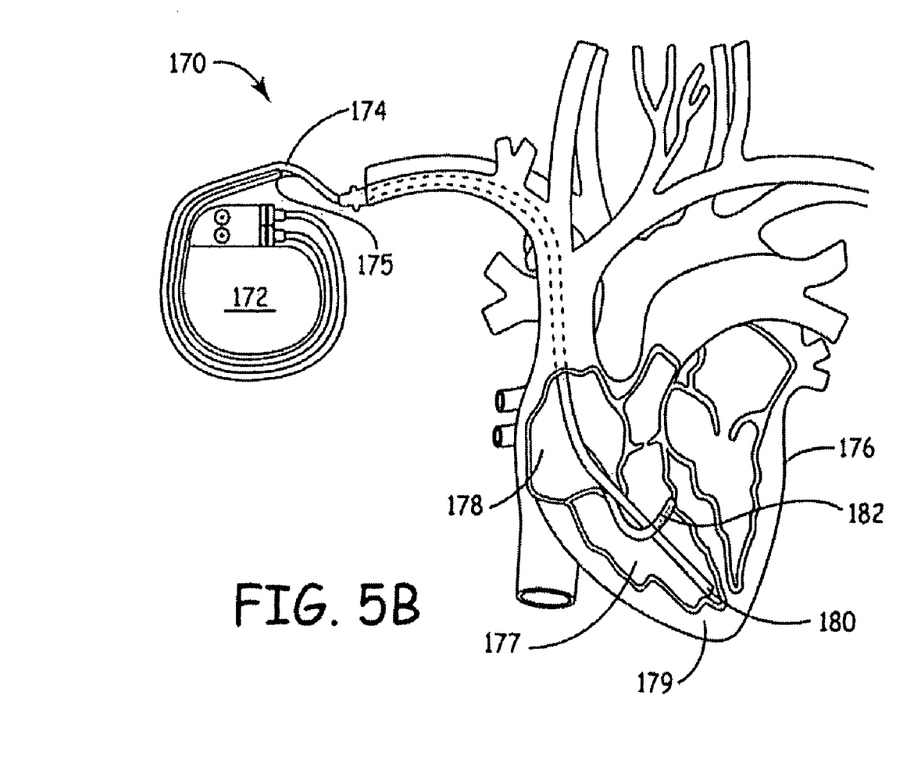
FIG. 5B is a schematic, cutaway view of a heart having an ISE pair lead disposed within and coupled to an implantable medical device (IMD)

FIG. 5B illustrates an implanted medical device (IMD) 170, which can be, for example, a pacemaker or an implantable cardio defibrillator. IMD 170 includes a housing or can 172 and two leads 174 and 175. Lead 174 extends into a heart 176, through right atrium 178 and right ventricle 177, to terminate in a conventional electrode 180 disposed against the right ventricle wall 179. Lead 175 also extends into heart 176 and terminated in an ISE pair 182 placed at a high blood flow site. The high blood flow site can be, for example, the right ventricular outflow tract (RVOT) or the super vena cava (SVC), to minimize thrombosis formation and tissue encapsulation. Placing a biochemical sensor at blood high flow region, like RVOT or SVC, advantageously avoids or at least reduces tissue encapsulation or thrombosis formation (as shown in FIG. 5A) on the sensor. Tissue encapsulation or thrombosis formation on the sensor surface will deleteriously creates extra diffusion barrier(s) for analytes to reach the sensor surface, thus delaying the sensor response to true analyte variation in the blood stream. The metabolism of encapsulated tissue/cells may also generate local analytes concentration, which may be quite different from the circulating blood. This causes sensor output irrelevant to the disease progression and sensor signal becomes unreliable.

Figure 6:
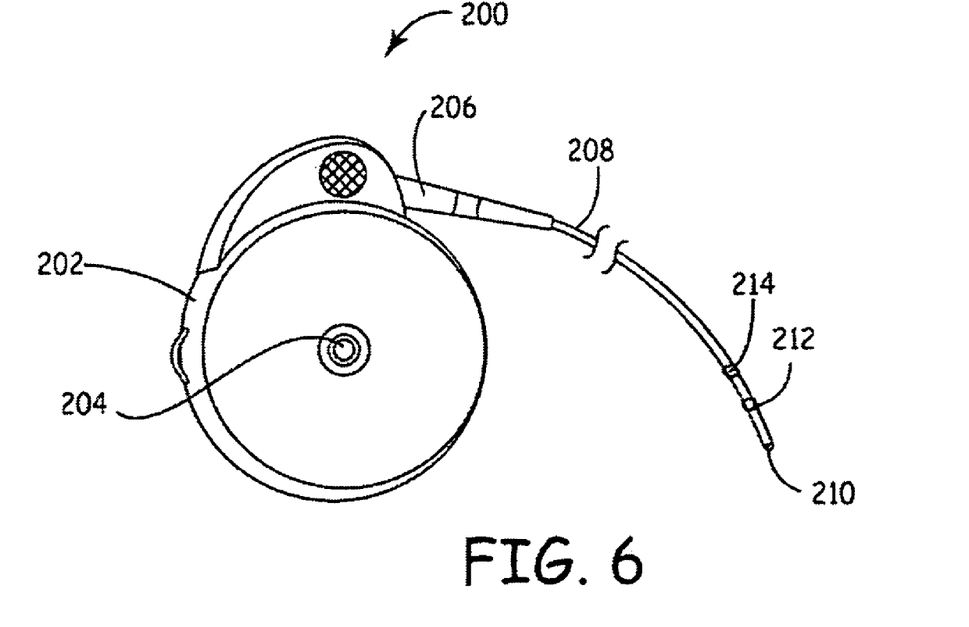
FIG. 6 is a schematic view of a drug delivery device controlled by an ISE pair.

FIG. 6 illustrates a drug delivery device 200 having a housing 202 and a seal or septum 204 for filling the device with the drug to be delivered. Device 200 also includes a tube 208 having a distal port 210 for delivering the drug and coupled to housing 202 with a strain relief 206. In this example of this aspect of the invention, an ISE pair including a Na ISE 212 and a target ISE is disposed on the drug delivery tube. In other embodiments, the ISE pair can be disposed on a separate lead, as illustrated in FIG. 5B.

Device 200 represents a drug delivery device generally, both external having an internal delivery tube, and implantable devices. Device 200 can be similar in some respects to externally worn insulin delivery devices. Device 200 may be similar in some respects to implantable drug delivery devices, such as the Synchromed drug delivery device (available from Medtronic, Minneapolis, Minn.). Device 200 can include a controller within for controlling the drug delivery responsive to the differential electrical potential from the ISE pair. The device may control a variable orifice opening, the opening and shutting of an open-shut valve, the delivery rate of a metering pump, and other delivery rate control devices well known to those skilled in the art. The drugs or substances delivered can be drugs previously discussed, including, for example, diuretics.

In another aspect of the present invention, self-plasticizing ISE membranes may be used. Plasticizers are typically used in ISE membranes and may form a considerable portion of (e.g. even half) of the membrane weight. The plasticizer allows the analyte to migrate through the ISE membrane. With time however, the plasticizer and the ionophore may both leach from the membrane. This may degrade the performance of the ISE over time.

Some embodiments of the present invention include an implantable ISE pair having ISE membranes that are self-plasticizing. Some embodiment methods include the in vivo measuring of ion ratios using a Na ISE as the reference electrode, where both ISE membranes have at least some self-plasticizing functionality. In some ISE membranes according to the present invention, there is no, or essential no unbound plasticizers in the ISE membranes.

According to this aspect of the invention, the present invention can provide a selective electrode for use in measuring the concentration of an ion in solution comprising an electrode polymer membrane which is selectively permeable to the substance to be measured, where the membrane is formulated from a polymer with a backbone, which may be an acrylate backbone and have a plurality of pendant lipophilic plasticizing groups.

The membrane can be formulated from a polymer having an acrylate backbone and a plurality of pendant lipophilic plasticizing groups to provide the polymer with a Tg of −10° C. or less. The Tg of the polymer can be measured directly using any suitable apparatus. The polymer Tg lies in the range from −10° C. to −70° C., or from −30° C. to −60° C., in some embodiments. The lipophilic plasticizing groups are $C_{3-7}$ alkyl groups in some polymers used in the present invention. Use of $C_{3-7}$ alkyl acrylates in the polymer can provide a polymer that is inherently soft and does not require added plasticizer, i.e. the polymer is in effect self-plasticizing, so that the problem of leaching of the plasticizer does not arise.

Materials such as ceramics, metal-oxides, glass, and polymers can be used in the membrane carrying the ionophore. Some polymers can include polyurethane, PVC, and silicone rubber. The polymer used according to the invention can have an acrylate backbone and can be a polymer or copolymer of one or more of the following monomers: propyl acrylate, butyl acrylate, pentyl acrylate, hexyl acrylate, heptyl acrylate. The polymer may be a homopolymer or may be a co-polymer including two or more different monomer units. The different monomer units may be derived from $C_{3-7}$ alkyl acrylates as described above or the polymer may include a minor proportion of other monomer units, for example up to 10% by weight of monomer units derived from lower ($C_1$ or $C_2$) alkyl acrylates or methacrylates, for example methyl methacrylate. In the case of $C_6$ or $C_7$ alkyl acrylates, it may be advantageous to use this monomer in admixture with a lower, for example $C_3$ or $C_4$ alkyl acrylate. For example, a mixture of 70% heptyl acrylate and 30% butyl acrylate may be used. Straight chain alkyl acrylates may be used. Branched chain alkyl acrylates or alpha or beta substituted monomers tend to produce a polymer of higher Tg than polymers produced from the corresponding straight chain or non-substituted monomer.

It may be desirable to adjust the hydrophobic/lipophobic balance (HLB) of the polymer so as to be compatible with a particular ionophore or other analyte receptor which it is desired to incorporate into the polymer. HLB can be adjusted by including monomers containing hydroxyl groups, for example hydroxy ethyl methacrylate.

The ionophore may be incorporated into the monomer mixture used to produce the polymer, thus trapping the ionophore in the polymer matrix. Alternatively the ionophore may be secured chemically by grafting to the polymer backbone. In general, the more hydrophilic the polymer, the more the ionophore will be subject to leaching in which case it is especially advantageous to graft the ionophore to the polymer backbone.

Good ISEs generally try to exhibit Nernstian response to the target ion concentration. In the present invention, for the sodium ISE, it may be desirable to have sub-Nernstian response. In particular, it may be desirable to have the sodium ISE exhibit a flater slope with respect to change in sodium concentration than normal, over the physiological range of sodium concentration, such that the body fluid sodium ion concentration changes do not follow the 59 mV slope, but rather a flater slope than normal. This would provide a more constant potential from the sodium ISE acting as the reference electrode.

Applicant believes that the sodium ISE may be made to exhibit sub-Nernstian response by making the polymeric membrane more hydrophilic than normal. This may be accomplished by the incorporation of hydroxyl groups into the polymer, as one example. Polymer chemists skilled in the art will know how to modify existing polymers to be more hydrophilic. Applicant also believes that the sodium ISE polymer may be adjusted to operate closer to, but under, the point of the Donnan exclusion failure. Some sodium ISEs have a molar ratio of ionophore to lipophilic salt of between about 1 and 1.1.

Some ISE membranes according to the present invention can include a polymer matrix, and active components such as ionophores, salt additives or enzymes that can enhance sensor stability and use life. Conventional sensor materials and components may include polyvinyl chloride, polyurethane, silicone rubber, and various kinds of plasticizers, lipophilic salt additives and ionophores incorporated within these polymers.

The ISE pairs can measure ion pairs of interest, for example, pH/Na+, Cl−/Na+, K+/Na+, etc. in vivo/ex vivo, either acutely or chronically. Some embodiments of the present invention include implanting multiple ion sensors at multiple sites, by comparing ion activity or ion pair ratio (e.g. $K^+/Na^+$), at the same time or different times (e.g., trending analysis), to analyze the function of the same organ at different parts: e.g., within the heart, at RVOT versus deep inside coronary sinus; or of different organs, e.g., heart versus kidney; or to analyze different media, e.g., venous blood versus arterial blood, or venous blood versus urine (for kidney function analysis), or to monitor tissue/organ disease progress, e.g., inside versus outside cancer tumor, or to put the sensor into artificial organs (e.g. heart, kidney or liver) to monitor these artificial organs' performance in vivo or ex vivo. The sensor may be used if the ratio of electrolyte pair is itself of interest or clinical importance. The sensor can also be used in the blood, in the kidney dialysis loop, in extracorporeal life support systems (e.g. heart-lung machines, dialysis machines), or even in instruments monitoring cell growth and death.

The present invention may be used in drug dosing: e.g., for administering spironolactone, ACE inhibitor and diuretics. Some examples of the invention may be used to provide warning of hyperkalimia/hypokalimia. Some devices and methods according to the present invention may be used to monitor organ status: e.g., heart infarction, remodeling, kidney failure, or hypertension. Sodium ISEs according to the present invention may be used as the reference electrode in various in vivo enzymatic biosensors to measure, for example, glucose, urea and creatinine.

The present invention also provides a method for detecting ischemia. When ischemia occurs, the drop in oxygen and rise in carbon dioxide leads to a rapid drop in pH. Applicant believes this drop in pH may be observed in both the arterial blood downstream of the blockage and somewhat in venous blood fed through arterial then venous capillaries near the blockage. After cell death has occurred, potassium may be released from the affected cells into the blood stream, increasing the potassium concentration the blood. The drop in pH, and/or increase in potassium, may thus be used as an indication of ischemia, in the heart, in the brain, and in other muscles and organs. In one example, a pH ISE/sodium ISE electrode pair can be used to monitor the pH in or near the heart over time, and generate and alarm or indication when a significant drop in pH has occurred. A measurement in pH near or within the heart can provide a good, undiluted, pH measurement. Some methods and systems include both the initial drop in pH and the later rise in potassium, in the generated indications.

One indication of ischemia can include storage of a marker or flag in an implanted medical device, for later reading by telemetry and transmittal to a physician. Another indication can include an immediate transmittal via wired or wireless communication to a device located outside of the patient's body, which may immediately alert the patient. This device can transmit the indication to a central location, for example, over telephone lines, for interpretation by a physician.

The pH and potassium levels may be tracked as a ratio or tracked effectively as the pH and potassium, where the sodium level is measured periodically and/or inferred in the ratios to determine the pH and potassium levels.

Ion-Selective Electrode Membrane Preparation

Ion-selective membranes may be prepared using methods well known to those skilled in the art. Recipes, materials, and methods are provided in the Fluka Chemica Selectophore catalog, available from Sigma-Aldrich Chemical. Some examples are given in PCT Publication No. WO 00/54039, herein incorporated by reference. Some information from WO 00/54039 is reproduced below.

Example 1

(Polymer Type I) Typical Recipe n-butyl acrylate (BA)=2.5 g
methylmethacrylate (MMA)=0.3 g
2,2'-azobisisobutyronitrile (AIBN)=0.003 g
benzene=3 ml
ionophore (e. G. acrylolamidobenzo-15-crown-5 or 18-crown-6)=0.1 G
measured polymer Tg=−29.4° C.

Procedure A: Polymerisation

The monomers, initiator and ionophore are mixed slowly with the solvent (benzene) and degassed with nitrogen for 10 minutes. The mixture is heated with stirring to 110° C. for 1 hour at which temperature it slowly thickens. The temperature is then lowered to about 70° C. which temperature is maintained for a further 6 hours to complete the reaction.

B. Isolation

About 5 ml of benzene is added to the cooled, sticky, clear, semi-solid and the mixture stirred vigorously. 1 ml of the clear sticky liquid produced is added to 100 mL of petroleum ether (either 60° C. or 80° C. boiling fraction) with vigorous stirring until the solvent becomes clear and a stick, glue like solid is obtained. The solvent is poured off and the solid washed with a further 20 ml of petroleum ether. The procedure is repeated with the remainder of the polymer solution until all of the polymer has been precipitated.

C. Purification

All of the precipitated polymer is redissolved in about 10 ml of 1,4-dioxane. 100 ml of distilled water is added to about 2 ml of polymer solution and a white sticky polymer appears. The procedure is repeated for the remainder of the polymer solution and all of the polymer portions are mixed and dried in a freeze drier for 2 hours. The whole of the polymer purification procedure as described above is repeated and the pure polymer is then dried in a freeze drier under a vacuum of 10-2 atmospheres for 24 hours. The final appearance of the polymer is usually a colorless, clear, elastic and sticky solid although on occasions it may appear slightly translucent. Yield 50 to 70%.

Possible Modifications

The following modifications may be made in the procedure described above as appropriate:
1. The solvent benzene (which is relatively toxic) may be replaced by ethyl acetate;
2. petroleum ether may be replaced by n-hexane;
3. Both the isolation and the purification steps may be omitted in which case the unpurified polymer mixture is diluted to the required concentration for direct film deposition.

Fabrication of Membrane for Potassium Selective Electrode

A cocktail of polymer type I (about 0.2 g of the polymer) containing the appropriate lipophilic anion (for details see later) is prepared by dissolving the various components in about 1 ml of dichloromethane. The cocktail is then poured onto a glass ring (QUICKFIT adapter) rested on a glass slide. The top of the ring is covered with a piece of filter paper and a heavy weight on top presses the paper against the ring. After 24 hours of evaporation in a fume cupboard, the whole is immersed in water for 2 hours following which it is possible to remove the membrane from the glass slide and the membrane is ready for testing.

Polymer Type I with Immobilized Potassium Ionophore 18C6 Membrane Recipe:
Non-plasticised polymer=0.15 g (BA=90 WT %, MMA=6.4 wt %)
Immobilized 18-crown-6=1.9 wt %
Potassium tetrakis(p-chlorophenyl borate)=1.7 wt % (60 mol %)
measured polymer TG<−29.4° C.

Polymer Type I with Immobilized Potassium Ionophore 15C5 Membrane Recipe:
Non-plasticised polymer=0.25 g (BA=88.6 wt %, MMA=7 wt %)
Immobilized 15-crown-5=3.8 wt %
Potassium tetrakis(p-chlorophenyl borate)=0.6 wt % (10 mol %)
measured polymer Tg=−20.9° C.

Polymer Type II Typical Recipe:
Inner layer: hydroxyethyl methacrylate=3 mg
2,2-dimethoxy phenylacetophenone=1 wt %
Ion-selective film: n-butyl acrylate=90 wt %
hexanedioldiacrylate=0.1-0.3 wt %
2,2-dimethoxy phenylacetophenone=1.6%.
Measured polymer Tg=−44.1° C.
Amount of ionophore varies depending on the type of ionophore.
Amount of lipophilic additive varies depending on the ionophore.

Procedure A. Fabrication of Polyhema Layer

The surface of a Ag/AgCl button is wiped clean of dust with absolute ethanol. A solution of hydroxyethyl methacrylate which contains 1 wt % of the photoinitiator 2,2-dimethoxy phenylacetophenone (DMPP) is prepared and 3 mg of this solution is deposited on the button using a Gilson pipet. Without delay the button is placed in a UV exposure unit (RS) and the unit is flashed with a stream of nitrogen before the lamp is switched on for a duration of about 5 minutes with continued flashing with nitrogen during which time polymerisation occurs. At the end of 5 minutes, polymerisation is completed to form a hard, glassy, transparent polymer film. The UV unit is switched off and the polyhydroxymethacrylate (polyhema) film rinsed with a little absolute ethanol. The film is dried at room temperature for several minutes before a drop of salt solution (depending on the sensor type) is added on the film and 2 hours are allowed for hydration.

B. Recipes for Ion-Selective Films

Depending on the type of ion sensing film, the monomer, ionophore and lipophilic additive used to prepare the ion-selective film can vary both in type and concentration as follows:

Monomers: n-butyl acrylate
methyl methacrylate
n-heptyl acrylate
cyanoethylacrylate
Ionophores: potassium: acrylamidobenzol 5-crown-5 (requires THF/benzene as solvent)
valimomycin
sodium: bis[(12-crown-4) methyl]dodecylmethylmalonate (Sodium Ionophore VI)
hydrogen: tridodecylamine (Hydrogen Ionophore I)
calcium: N,N-dicyclohexyl-N'N'-dioctadecyl-3-oxapentamide (Calcium Ionophore IV)
lithium: 6,6-dibenzyl-14-crown-4 (Lithium Ionophore VI)
Additives: potassium tetrakis(p-chlorophenyl)borate
sodium tetrakis(trifluoromethylphenyl)borate.

Details of the recipes for various photocured ion-selective films are given below.

Fabrication of Ion-Selective Film

A cocktail which contains the monomer or monomers, cross-linker hexanedioldiacrylate, photoinitiator DMPP, ionophore and lipophilic additive is prepared and all of the components should form a homogeneous solution. About 10 µl of this solution is drop coated on top of the hydrated polyhema layer with a Gilson pipet. The button is then exposed to UV radiation in an UV exposure unit for about 6 minutes (for most cross-linked acrylate films) under continuous purging with nitrogen gas. The film formed is usually clear, soft and tacky but elastic. The surface of the film is rinsed with several drops of petroleum ether to remove unreacted substances.

The solid state electrode is ready for testing after encapsulation with ARALDITE epoxy or fixed on to a static cell with an O-ring seal.

Possible Modifications Alternative initiators can be used including benzoyl peroxide and benzophenone.

Example 1

Potassium Ion-Selective Solid-State Electrode Based on Polymer Type II with Immobilized 15C5 Evaluated Under Constant Exposure of 0.1M KCl Polyhema Layer hydroxyethyl methacrylate=6 mg
2,2-dimethoxy phenylactophenone=1 wt %
Duration of UV irradiation=10 minutes
Conditioned in KCl for 2 hours
Composition of photocured membrane (total weight 26 mg):
n-butyl acrylate=83.9 wt %
methyl methacrylate=12 wt %
AAB 15C5=2.5 wt % (in 90 µl THF)

potassium tertakis(p-chlorophenyl borate)=0.3 wt % (8.6 mole %)
2,2-dimethoxy phenylacetophenone=0.9 wt %
UV exposure time=40 minutes
measured polymer Tg<−20.9° C.

Example 2

Potassium Ion-Selective Solid-State Electrode Based on Polymer Type II with Entrapped Valinomycin Polyhema Layer hydroxyethyl methacrylate=3 mg
2,2-dimethoxy phenylactophenone=1 wt %
Duration of UV irradiation=7 minutes
Conditioned in KCl for 2 hours
Composition of ion-selective membrane (total weight 15 mg):
n-butyl acrylate=96 wt %
hexanediol diacrylate=0.09 wt %
valinomycin=2.1 wt %
potassium tertakis(p-chlorophenyl borate)=0.59 wt % (60 mole %)
2,2-dimethoxy phenylacetophenone=1 wt %
UV exposure time=7 minutes
measured polymer Tg=42.6° C.

Example 3

Sodium Ion-Selective Solid-State Electrode Based on Polymer Type II with Entrapped Sodium Ionophore IV Polyhema Layer hydroxyethyl methacrylate=3 mg
2,2-dimethoxy phenylactophenone=1 wt %
Duration of UV irradiation=7 minutes
Conditioned in NaCl 0.1M for 2 hours
Composition of Ion-Selective Film (Total Weight 11 mg):
n-butyl acrylate=94.7 wt %
hexanediol diacrylate=0.11 WT %
2,2-dimethoxy phenylacetophenone=0.72 wt %
Na ionophore IV=4.3 WT %
sodium tertakis(trifluorophenyl borate)=0.22 wt % (9 mole %)
Duration of irradiation=8 minutes
measured polymer TG=42.6° C.

The above examples of ISE membrane recipes are only non-limiting examples, with many other examples well known to those skilled in the art.

Thus, embodiments of the ION SENSOR FOR LONG TERM USE IN COMPLEX MEDIUM are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method for detecting ischemia comprising:
obtaining a differential electrical potential between an implanted electrode pair in a human body, the electrode pair including a first ion selective electrode (ISE) and a sodium ISE, wherein first ISE is a potassium ISE; and
employing an implanted medical device to generate an indication of ischemia at least in part as a function of a change in the differential electrical potential over time, wherein the change is a rise in a ratio of potassium to sodium over time.

2. A method according to claim 1, in which the obtaining includes the electrode pair being implanted in a heart in the human body.

3. A method according to claim 1, in which the ischemia detected is a cardiac infarction.

4. A method according to claim 1, in which the ischemia detected takes place in a brain in the human body.

5. A method according to claim 1, wherein at least one of the first ISE and the sodium ISE are adapted to be disposed at least partially in a region of relatively high fluid flow.

6. A method according to claim 5, wherein said region of relatively high fluid flow comprises a portion of: a Superior Vena Cava vessel, an Inferior Vena Cava vessel, a right ventricular outflow tract.

* * * * *